(12) United States Patent
Lee et al.

(10) Patent No.: US 6,767,366 B2
(45) Date of Patent: Jul. 27, 2004

(54) SPINAL PROSTHETIC IMPLANT AND INSERTION INSTRUMENT

(75) Inventors: Choon Sung Lee, 808 Misung Apt. 2 Dong, 414, Apkujung-dong, Kangnam-ku, Seoul (KR); Seayoung Ahn, Bethesda, MD (US); Sang Soo Park, Seoul (KR); Sang Il Jung, Seoul (KR); Jin Yong Lim, Seoul (KR); Jin Soon Kim, Seoul (KR)

(73) Assignees: Solco Biomedical Co., Ltd., Kyungki-do (KR); Choon Sung Lee, Kangnam-Ku (KR)

( * ) Notice: Subject to any disclaimer, the term of this patent is extended or adjusted under 35 U.S.C. 154(b) by 0 days.

(21) Appl. No.: 10/073,080

(22) Filed: Feb. 12, 2002

(65) Prior Publication Data

US 2003/0114931 A1 Jun. 19, 2003

(30) Foreign Application Priority Data

Dec. 13, 2001 (KR) ........................................ 2001-79006

(51) Int. Cl.[7] .............................. A61F 2/44; A61B 17/70
(52) U.S. Cl. ................................. 623/17.16; 623/17.11; 606/61
(58) Field of Search ........................ 606/99, 61, 86–92, 606/53, 72, 73, 81–84; 623/17.11–17.16

(56) References Cited

U.S. PATENT DOCUMENTS

| | | | |
|---|---|---|---|
| 5,800,550 A | | 9/1998 | Sertich |
| 5,888,224 A | * | 3/1999 | Beckers et al. ........... 623/17.16 |
| 6,290,724 B1 | * | 9/2001 | Marino ...................... 623/17.11 |
| 6,582,431 B1 | * | 6/2003 | Ray ............................. 606/61 |

* cited by examiner

Primary Examiner—David J. Isabella
(74) Attorney, Agent, or Firm—Harness, Dickey & Pierce, PLC

(57) ABSTRACT

The present invention discloses a prosthetic implant and an insertion instrument for inserting the prosthetic implant between adjacent vertebrae. The prosthetic implant in accordance with the present invention includes a housing for being packed with bone chips, an inserting hole formed at a first end of the housing, through which an insertion instrument can be inserted, and a connection recess formed on inner surface of the housing around the inserting hole, on which the insertion instrument is stably placed. The insertion instrument in accordance with the present invention includes a connection member having a connection chip at a first end, a rotating means for rotating and returning the connection member at a predetermined angle. In accordance with the present invention, the insertion instrument can be separated from the prosthetic implant by rotation of only one time after the prosthetic implanted is completely inserted, so that the operation process of implanting the prosthetic implant is easy and safe. Further, the prosthetic implant in accordance with the present invention safely and stably fixed between the adjacent vertebrae because projections are formed at the upper end and lower end of the prosthetic implant respectively.

10 Claims, 8 Drawing Sheets

SPINAL PROSTHETIC IMPLANT AND INSERTION INSTRUMENT

FIELD OF THE INVENTION

The present invention relates to a spinal prosthetic implant for fusing adjacent vertebrae and an insertion instrument for implanting the same.

DESCRIPTION OF THE PRIOR ART

The vertebral column extends from the skull to the pelvis and is made up of 32~35 individual bones (vertebra) and intervertebral disks between adjacent vertebrae. Recently, where that a patient suffers from sciatica, lumbago or spinal fracture, vertebral column union administration of medicine is performed. That is, damaged or injured natural discs are removed from the vertebral column of humans and adjacent vertebrae are fused by implanting substitutes such as a spinal prosthetic implant.

FIG. 1 is a side view of a spinal prosthetic implant in accordance with the conventional art, the prosthetic implant is generally constructed of a housing of a hollow plunger cylinder shape and bone chips taken from the patient or other human beings, or a substitute thereof. The bone chips or substitutes thereof are packed into an internal cavity of the housing formed in the shape of a hollow cylinder so as to promote and stabilize the fusion of adjacent vertebrae.

The prosthetic implant is directly implanted into the inserting space formed in the vertebral column. The prosthetic implant 100 is inserted using an insertion instrument and then the insertion instrument is removed without moving the prosthetic implant 100 so as to promote internal growth of adjacent spine backbone.

The prosthetic implant, called a cage, is constructed of various shapes such as ring illustrated in FIG. 1, a rectangular, a spiral cylinder and so on.

The prosthetic implant 100 in accordance with the conventional art usually has a nut hole 101. The prosthetic implant 100 is implanted into the inserting space formed in the vertebral column by sequentially carrying out the steps of screwing a bolt of an insertion instrument into the nut hole 101 of the prosthetic implant 100, inserting and placing the prosthetic implant 100 into the inserting space between vertebrae and unscrewing the bolt of the insertion instrument.

However, that kind of implanting method is inconvenient because the bolt of the insertion instrument must be rotated several times for separating the insertion instrument from the prosthetic implant 100.

Further, the prosthetic implant of the conventional art has a projection on an upper and a lower surfaces thereof respectively to protect the prosthetic implant from slipping forward (the abdomen) or backward (the back). However, because the projection has no specific direction, the conventional prosthetic implant tends to be easily slip in response to the fixed force of downward load.

SUMMARY OF THE INVENTION

The present invention has been made in an effort to solve the above problems.

It is, therefore, an object of the present invention is to provide a prosthetic implant that can be easily, stably and rapidly be inserted into an inserting space of a human body during an operation for implanting the prosthetic implant.

It is, therefore, another object of the present invention is to provide a prosthetic implant that can be stably fixed after the prosthetic implant is implanted into a human body.

It is, therefore, still another object of the present invention to provide an insertion instrument that is capable of stably fixing a prosthetic implant during the implanting operation so that the prosthetic implant is secure.

In accordance with a first preferred embodiment of the present invention, there is provided a prosthetic implant comprising a housing for being packed with bone chips; an inserting hole formed at a first end of the housing, through which an insertion instrument can be inserted; and a connection recess formed on inner surface of the housing around the inserting hole, on which the insertion instrument is stably placed.

In accordance with the first preferred embodiment of the present invention, the inserting hole and the connection recess have an oblong or rectangle shape and the connection hole is concentric with the inserting hole.

In accordance with the first preferred embodiment of the present invention, an uneven section is formed at a second end of the housing for fixing the prosthetic implant during an implanting operation, the second end being opposite to the first end.

In accordance with the first preferred embodiment of the present invention, a plurality of projections having an inclined plane are formed at an upper end and a lower end of the housing, respectively, and the inclined planes of the projections formed in opposite sides from the center of the housing are opposite slope to each other in direction.

In accordance with the first preferred embodiment of the present invention, the inclined planes of the projections slope down toward the center of the housing.

In accordance with the first preferred embodiment of the present invention, the inclined planes of the projections slope up toward the center of the housing.

In accordance with the first preferred embodiment of the present invention, the housing has sliding planes at the first end.

In accordance with a second preferred embodiment of the present invention, there is provided an insertion instrument for inserting a prosthetic implant between adjacent vertebrae, comprising: a connection member having a connection chip at a first end; and a rotating means for rotating and returning the connection member at a predetermined angle.

In accordance with the second preferred embodiment of the present invention, the rotating means includes a supporting member having a hollow through which the connection member is inserted; and an elastic member elastically supported by the supporting member for giving elastic force to the connection member.

In accordance with the second preferred embodiment of the present invention, the rotating means further includes a handle being connected to a second end of the connection member for rotating the connection member, the second end being opposite to the first end.

In accordance with the second preferred embodiment of the present invention, the supporting member has an elastic member receiving recess at an end for receiving the elastic member.

In accordance with the second preferred embodiment of the present invention, the elastic member is a leaf spring.

In accordance with the second preferred embodiment of the present invention, the elastic member is a disk shape having a hole in the center and has a protruded portion around the hole.

In accordance with the second preferred embodiment of the present invention, the connection chip has an oblong or rectangle shape.

In accordance with the second preferred embodiment of the present invention, the handle has an impacting section at an end for striking the handle while inserting the prosthetic implant between adjacent vertebrae.

BRIEF DESCRIPTION OF THE DRAWINGS

The above and other objects and features of the present invention will become apparent from the following description of preferred embodiments taken in conjunction with the accompanying drawings, in which.

DETAILED DESCRIPTION OF THE INVENTION

The invention may be better understood by a description of one embodiment with reference to the attached drawings.

Figure 1:
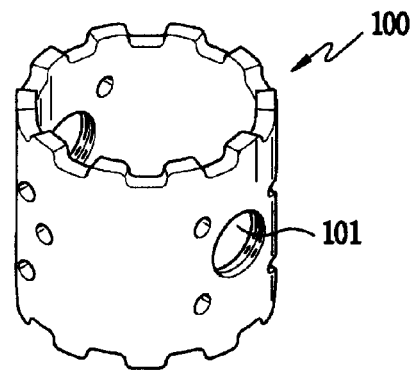
FIG. 1 is a perspective view of a prosthetic implant in accordance with a conventional art.
Figure 2:
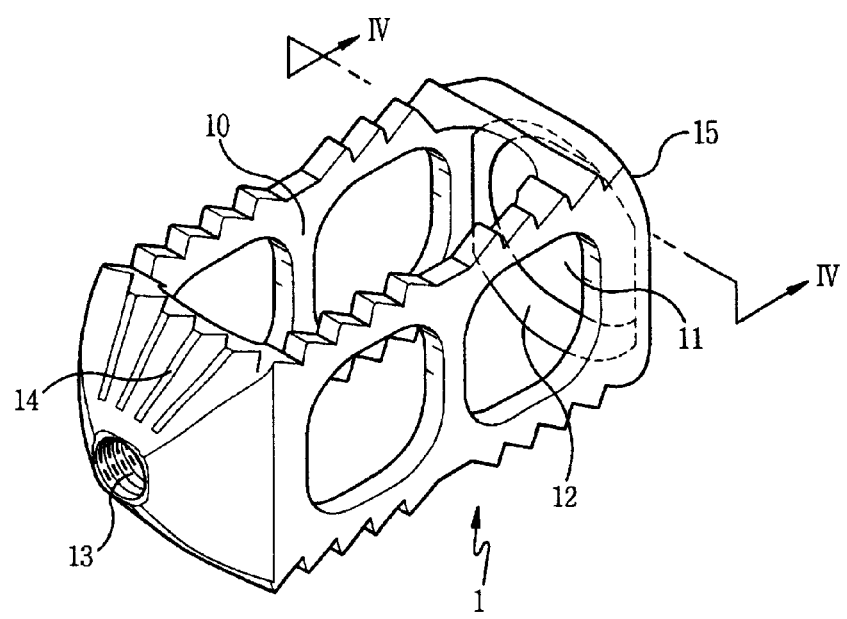
FIG. 2 is a perspective view of a prosthetic implant in accordance with a preferred embodiment of the present invention.

As shown in FIG. 2, prosthetic implant 1 in accordance with the present invention has a housing 10 and an inserting hole 11 at a first end of the housing 10 and a connection recess 12 (shown in FIG. 4) on an inner surface of the housing 10 around the inserting hole 11.

Figure 3:
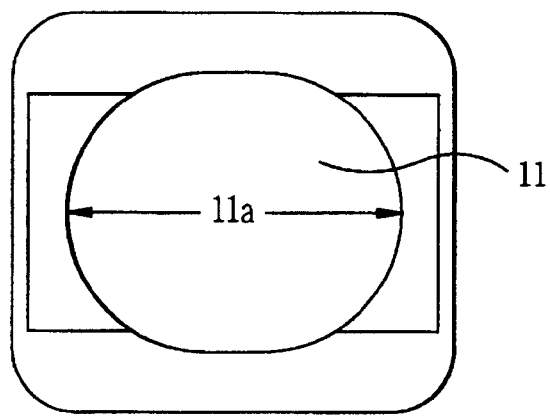
FIG. 3 is a rear view of the prosthetic implant shown in FIG. 2.
Figure 4:
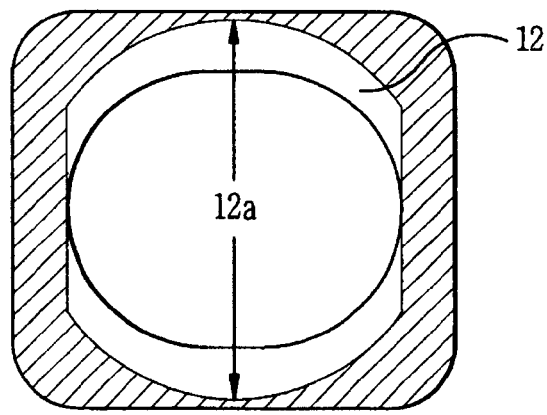
FIG. 4 is a cross-sectional view taken from along the line IV—IV in FIG. 2.

As shown in FIG. 3, the inserting hole 11 has an elongated hole having an oblong or rectangular shape. Further, as shown in FIG. 4, the connection recess 12 is formed to have an oblong shape similar to the inserting hole 11 and is concentric with the inserting hole 11. Further, the connection recess 12 is rotated at a certain angle, for example 90°, from the inserting hole 11.

The inserting hole 11 and the connection recess 12 are not limited to an elongated hole of an oblong or rectangle shape. Further, a long axis 11a of the inserting hole 11 is formed in a horizontal direction and a long axis 12a of the connective groove 12 is formed in a perpendicular direction to the long axis 11a.

Further, the prosthetic implant in accordance with the present invention has a nut hole 13 at a second end of the housing 10, in which the second end is opposite to the first end. The nut hole 13 is used to remove the prosthetic implant from the adjacent vertebrae in case the prosthetic implant 10 is damaged or broken after being implanted. Uneven section (prominence and depression) 14 is formed on an outer surface of the housing 10 near the nut hole 13 to fix it as the prosthetic implant is inserted into the inserting space between adjacent vertebrae at a first time. The prominence and depression/uneven section 14 is formed in a vertical direction so as to protect the prosthetic implant 10 from slipping out from the vertebra (human body). As a result, the prosthetic implant is stably placed and fixed.

Figure 7:
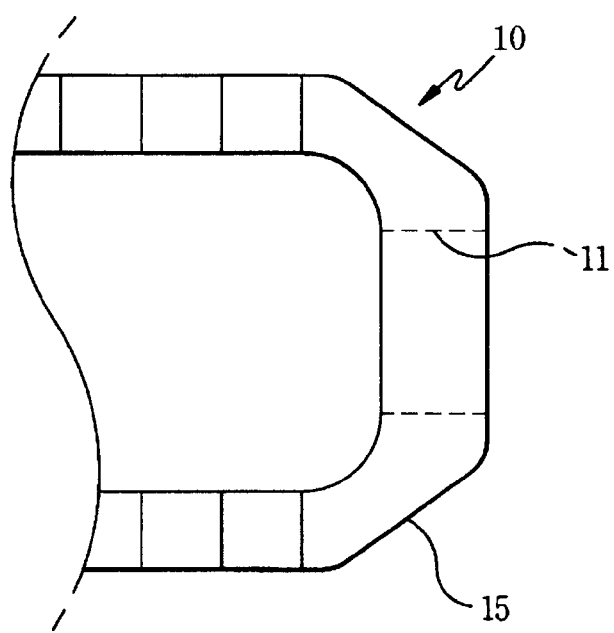
FIG. 7 is a partial plane view of a prosthetic implant in accordance with the present invention.

Further, as shown in FIG. 7, the prosthetic implant has a sliding plane 15 at the end portion where the inserting hole 11 is formed, so that the sliding plane 15 of the prosthetic implant 10 placed on a human body may be used to guide another prosthetic implant that is placed later where a plurality of prosthetic implants are implanted.

Figure 5:
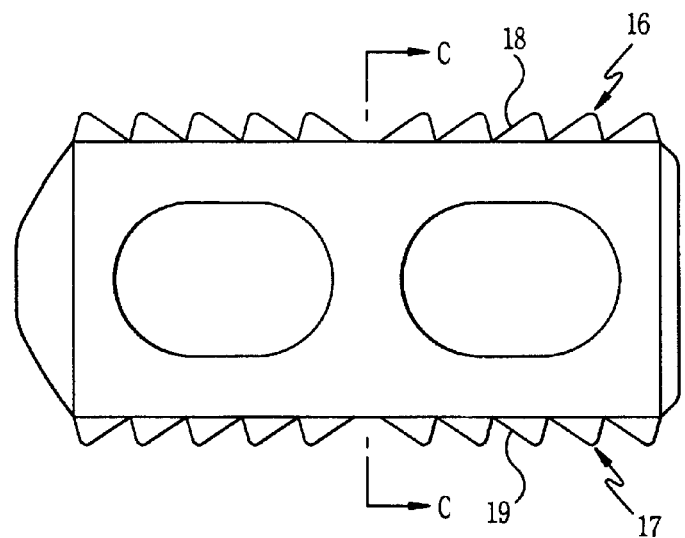
FIG. 5 is a front view of a prosthetic implant in accordance with a preferred embodiment of the present invention.

A plurality of projections 16,17 is formed at an upper end and a lower end of the housing 10 so as to support adjacent vertebrae. As shown in FIG. 5, the projections 16, 17 have inclined planes 18, 19. The incline direction of the inclined planes 18, 19 formed on one side (left side) of the center line C is opposite to incline direction of the inclined planes 18, 19 formed at the other side (right side) of the center line C. The inclined planes 18, 19 slope toward the center of the housing 10. Further, projections 16, 17 have pointed tips so as to be in the shape of a triangle. Accordingly, the prosthetic implant in accordance with the present invention can securely support the adjacent vertebrae when the prosthetic implant is implanted between adjacent vertebrae.

Figure 6:
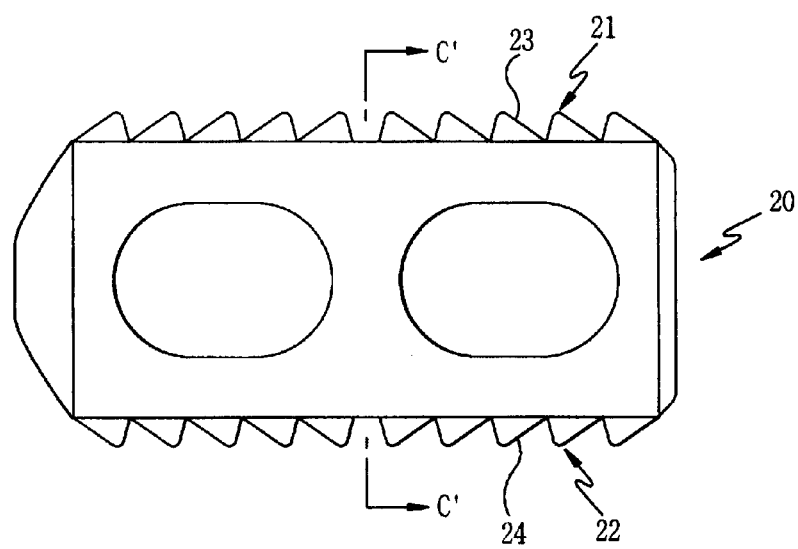
FIG. 6 is a front view of a prosthetic implant in accordance with another preferred embodiment of the present invention.

FIG. 6 is showing another embodiment of the present invention where projections 23, 24 have inclined planes 21, 22 which slope up toward the center of the housing 10 contrary to the direction of the projections 16, 17 in FIG. 5.

As shown in FIG. 5 and FIG. 6, the projections 16, 17, 23, 24 formed on opposite sides from the center of the housings 10, 20 have inclined planes with slopes in opposing directions. Accordingly, the prosthetic implant in accordance with the present invention can be stably secured to the adjacent vertebrae and will not easily shift.

Figure 8:
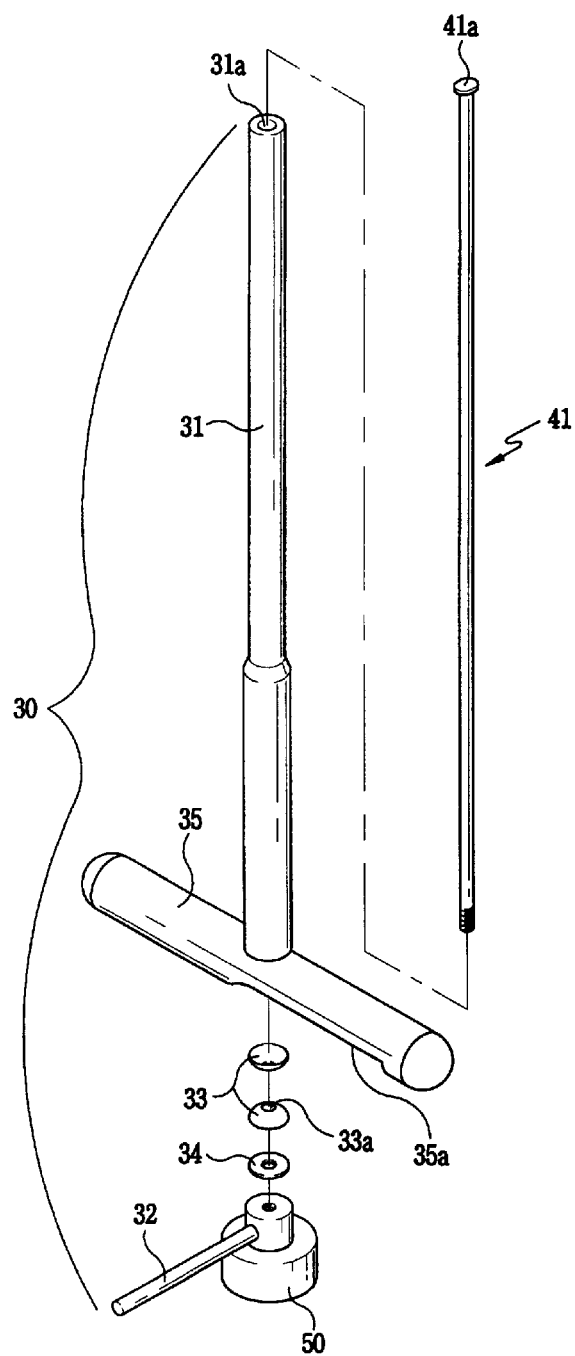
FIG. 8 is a perspective view showing a disassembled insertion instrument in accordance with the present invention.

Now, an insertion instrument in accordance with the present invention will be described below with reference to FIG. 8.

The insertion instrument is used for implanting the aforedescribed prosthetic implant between adjacent vertebrae. The insertion instrument in accordance with the present invention includes a connection member 41 having a connection chip 41a at first end (front end) thereof and a rotating means 30 for rotating the connection member 41 at a certain angle and returning it.

The connection member 41 has a stick shape and the connection chip 41a has a shape of an elongated oblong or rectangular hole similar to the shape of the inserting hole 11 so as to be inserted through the inserting hole 11.

The rotating means 30 comprises a supporting member 31 of cylinder shape having a hollow 31a in the center so that the connection member 41 can be inserted through the hollow, an elastic member 33 which is elastically supported by the supporting member 31 and connected with the second end (back end) of the connection member 41, and a handle for rotating the connection member 41 inserted through the supporting member 31.

The connection member 41 and the handle 32 are secured to each other using a screw. The hollow 31a formed in the supporting member 31 is formed to be smaller than the connection chip 41a so that the connection chip 41a should not be inserted into the hollow 31a but exposed outside the hollow 31 to be contacted to a first end (front end) portion of the supporting member 31.

The elastic member 33 is a disk type leaf spring having a hole 33a at the center to be inserted or penetrated by the connection member 41. Further the center portion around the hole 33a is protruded. However, the elastic member 33 is not limited to the disk type leaf spring but other shape of leaf spring or coil spring can be used as the elastic member.

A bar 35 is perpendicularly attached to a second end (back end) of the supporting member 31 so as to give convenience to an operating person who implants the prosthetic implant. Therefore, the bar 35 and the supporting member 31 are forming a "T" shape. Further, a handle 32 is connected to the connection member 41 being perpendicular to each other but is parallel with the bar 35. The bar 35 has a trench into which the handle 32 is placed. The handle 32 is rotated only in one direction.

The handle 32 also has an impacting section 50 at upper portion to give a blow to the prosthetic implant during inserting the prosthetic implant into an inserting space in the spine column.

Figure 9:
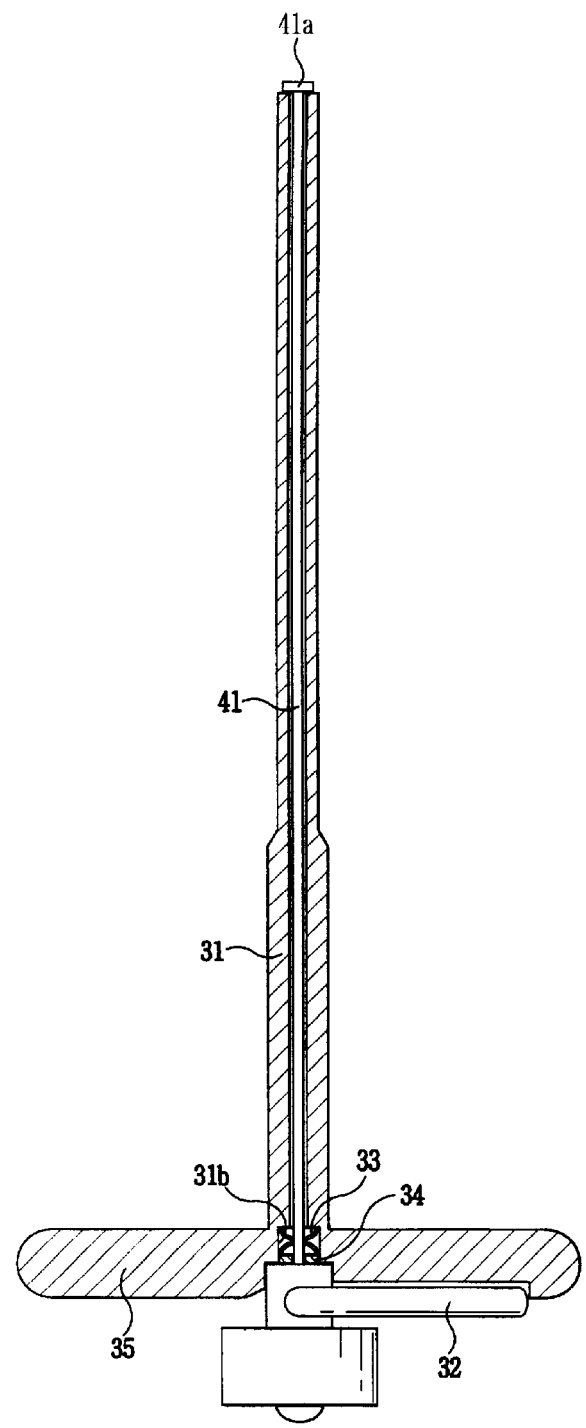
FIG. 9 is a cross-sectional view showing an assembled insertion instrument in accordance with the present invention.

FIG. 9 is a cross-sectional view of the insertion instrument in accordance with the present invention. As shown in FIG. 9, an elastic member receiving recess 31b is formed on a lower surface of a second end (back end) of the supporting member 31.

A method of assembling the insertion instrument in accordance with the present invention will be described below.

The second end of the connection member 41 is inserted through the hollow 31a of the supporting member 31, and then penetrates the hole 33a of the elastic member 33 and the washer 34. Finally, the handle 32 is attached to the second end of the connection member 41, so that the elastic member 33 and the washer 34 are inserted in the elastic member receiving recess 31b.

At this time, the connection chip 41a is not inserted into the supporting member 31 but exposed outside of the supporting member 31. The elastic member 33 gives elastic force to the connection member 41, so that the connection chip 41a connected to the connection member 41 can be slightly moved forward and backward.

A method for implanting the prosthetic implant as shown in FIG. 2 with the insertion instrument will be described.

Figure 10:
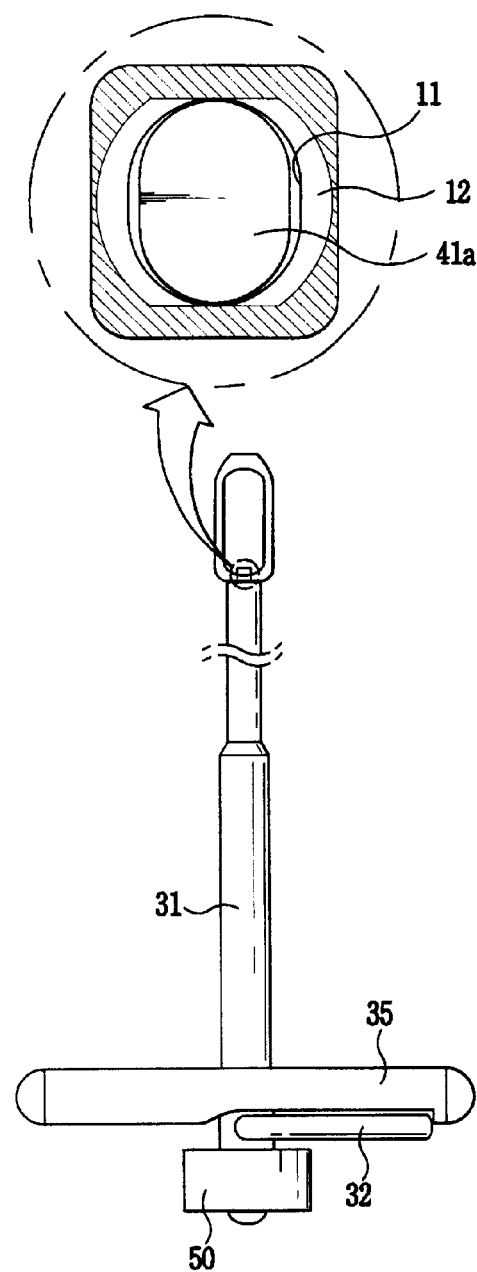
FIG. 10 is a front view showing an insertion instrument that a connection chip is inserted thereinto.
Figure 11:
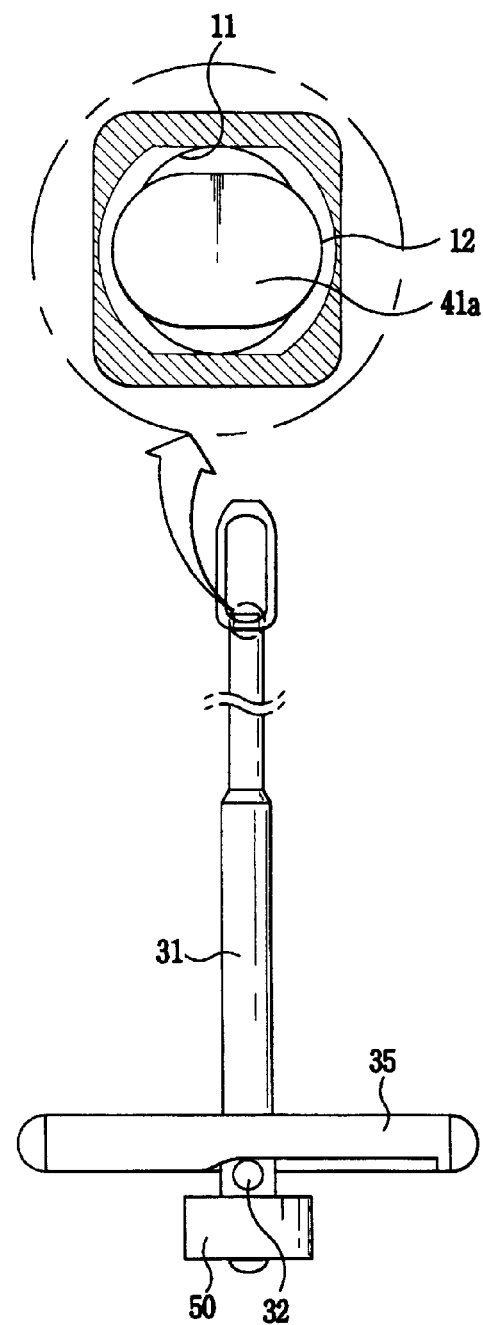
FIG. 11 is a front view showing an insertion instrument and prosthetic implant after the connection chip is inserted into the prosthetic implant by rotating a handle of the insertion instrument in accordance with the present invention.

First, the connection chip 41a is inserted through the inserting hole 11 formed on the housing 10 of the prosthetic implant. The shape of the connection chip 41a is similar to the inserting hole 11 as shown in FIG. 10. Accordingly, the connection chip 41a can be easily inserted.

Next, the connection chip 41a is rotated at a right angle by rotating the handle 32 placed in parallel with the bar 35 at a right angle so that the connection chip 41a is safely received in the connection recess 12 formed inside the prosthetic implant.

Next, an operator holds the insertion instrument, places and inserts the prosthetic implant between adjacent vertebrae of the human body by striking the impacting section 50 connected to the handle 32.

Finally, after the prosthetic implant is inserted into the exactly right position, the insertion instrument is separated from the prosthetic implant by returning the handle 32 so that the connection chip 41a is rotated in reverse at a right angle. The insertion instrument is then extracted.

In accordance with the present invention, the insertion instrument can be separated from the prosthetic implant by rotating only one time, so that the operation process of implanting the prosthetic implant is easy and safe.

Further, the inserted prosthetic implant is secured while separating the insertion instrument from the prosthetic implant after implanting the prosthetic implant between adjacent vertebrae.

Further, the prosthetic implant in accordance with the present invention allows an implant to be safely and stably fixed between adjacent vertebrae because projections formed at the upper end and lower end of the prosthetic implant, respectively, secure the position of the implant The invention may be embodied in other specific forms without departing from the sprit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. Prosthetic implant for fusing adjacent vertebrae, comprising:
   a housing;
   a non-circular inserting hole formed at a first end of the housing, through which an insertion instrument can be inserted; and
   a non-circular connection recess formed on an inner surface of the housing and concentric with the inserting hole on a common center line, on which the insertion instrument is stably placed, wherein the connection recess and the inserting hole are rotatably displaced with respect to each other at a fixed angle along the common line.

2. The prosthetic implant in accordance with claim 1, wherein the inserting hole has an oblong shape.

3. The prosthetic implant in accordance with claim 1, wherein the housing includes an uneven section formed at a second end of the housing for fixing the prosthetic implant during implanting operation, the second end being opposite to the first end.

4. The prosthetic implant in accordance with claim 2, wherein the housing includes an uneven section formed at a second end of the housing for fixing the prosthetic implant during implanting operation, the second end being opposite to the first end.

5. The prosthetic implant in accordance with claim 3, wherein the housing includes a plurality of projections formed on an external surface, said plurality of projections including a first set of projections formed near the first end of the housing and of a first incline, and a second set of projections formed near the second end of the housing and having a second incline opposing the incline of said first set of projections.

6. The prosthetic implant in accordance with claim 1, wherein the first end of the housing includes a plurality of converging planar elements.

7. The prosthetic implant in accordance with claim 1, wherein the inserting hole has a rectangular shape.

8. The prosthetic implant in accordance with claim 1, wherein the connection recess has a rectangular shape.

9. The prosthetic implant in accordance with claim 1, wherein the connection recess has an oblong shape.

10. The prosthetic implant in accordance with claim 1, wherein the inserting hole is rotatably disposed at an angle of 90° with respect to the connection recess.

* * * * *